United States Patent [19]
Lurquin et al.

[11] Patent Number: 5,587,289
[45] Date of Patent: Dec. 24, 1996

[54] ISOLATED NUCLEIC ACID MOLECULES WHICH ARE MEMBERS OF THE MAGE-XP FAMILY AND USES THEREOF

[75] Inventors: Christophe Lurquin; Thierry Boon-Falleur, both of Brussels, Belgium

[73] Assignee: Ludwig Institute for Cancer Research, New York, N.Y.

[21] Appl. No.: 403,388

[22] Filed: Mar. 14, 1995

[51] Int. Cl.$^6$ .................... C12Q 1/68; C07H 21/02; C07H 21/04; C12N 15/70

[52] U.S. Cl. .................... 435/6; 536/23.1; 435/320.1; 435/240.2; 435/252.3

[58] Field of Search .................... 536/23.1; 435/6, 435/91.2, 320.1, 240.2, 252.3

[56] References Cited

U.S. PATENT DOCUMENTS

| | | | |
|---|---|---|---|
| 5,342,774 | 8/1994 | Boon et al. | 435/240.2 |
| 5,405,940 | 4/1995 | Boon et al. | 530/328 |
| 5,462,871 | 10/1995 | Boon-Falleur et al. | 435/240.2 |

FOREIGN PATENT DOCUMENTS

| | | | |
|---|---|---|---|
| WO9220356 | 11/1992 | WIPO | A61K 35/14 |
| WO9405304 | 3/1994 | WIPO | A61K 35/16 |
| WO9423031 | 10/1994 | WIPO | C12N 15/12 |
| WO9504542 | 2/1995 | WIPO | A61K 38/00 |
| WO9504817 | 2/1995 | WIPO | C12N 5/08 |
| WO9521630 | 8/1995 | WIPO | A61K 48/00 |
| WO9525530 | 9/1995 | WIPO | A61K 38/00 |
| WO9525739 | 9/1995 | WIPO | C07K 7/00 |
| WO9525740 | 9/1995 | WIPO | C07K 7/00 |

OTHER PUBLICATIONS

Van der Bruggen et al. (1991) *Science* 254:1643–7.
Zakut et al. (1993) *Cancer Res.* 53:5–8.
Van der Bruggen et al. (1994) *Eur. J. Immunol.* 24:3038–43.
Imai et al. (1995) *Gene* 160:287–90.
Van den Eynde (1995) *J. Exp. Medicine* 182:689–98.
Toh et al. (1995) *Japanese J. Cancer Res.* 86:714–7.
Anichini et al. (1996) *J. Immunol.* 156:208–17.
Traversari et al. (1992) *J. Exp. Medicine* 176:1453–7.
Gaugler et al. (1994) *J. Exp. Medicine* 179:921–30.
Coulie et al. (1994) *J. Exp. Medicine* 180:35–42.
Coulie et al. (1995) *Proc. Natl. Acad. Sci. USA* 92:7976–80.
De Smet et al. (1995) *Immunogenetics* 42:282–90.
Muscatelli et al. (1995) *Proc. Natl. Acad. Sci. USA* 92:4987–91.

*Primary Examiner*—W. Gary Jones
*Assistant Examiner*—Amy Atzel
*Attorney, Agent, or Firm*—Felfe & Lynch

[57] ABSTRACT

The invention relates to members of the MAGE-Xp family of nucleic acid molecules. These molecules differ from the previously described MAGE nucleic acid molecules in that members of the MAGE-Xp family do not hybridize to the previously identified MAGE sequences. Further, the members of the MAGE-Xp family are found on the Xp arm of the X chromosome rather than on the Xq chromosome, as was the case with the previously identified MAGE genes.

12 Claims, No Drawings

5,587,289

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 1866 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GAGTGTTGCA  ACTGGGCCTG  GCATGTTTCA  GCGTGGTGTC  CAGCAGTGTC  TCCCACTCCT      60

TGTGAAGTCT  GAGGTTGCAA  AAGGACTGTG  ATCATATGAA  GATCATCCAG  GAGTACAACT     120

CGAAATTCTC  AGAAACAGG   ACCTTGATGT  GAGAGGAGCA  GGTTCAGGTA  AACAAAGGGC    180

GAGGACCCGA  GCGAGCTTAA  GGCCAGTGGG  GTGCAGCGTC  TGGTCAGCCG  AGGGTGAATT    240

CTCAGGACTG  GTCGGGAGTC  AAGGTGCCAC  ATCTCCTGCC  TTTCTGCTCA  CTTTCCTGCC    300

TGTTTTGCCT  GACCACAGCC  ATCATGCCTC  GGGGTCAGAA  GAGTAAGCTC  CGTGCTCGTG    360

AGAAACGCCG  CAAGGCGCGA  GAGGAGACCC  AGGGTCTCAA  GGTTCGTCAC  GCCACTGCAG    420

CAGAGAAAGA  GGAGTGCCCC  TCCTCCTCTC  CTGTTTTAGG  GGATACTCCC  ACAAGCTCCC    480

CTGCTGCTGG  CATTCCCCAG  AAGCCTCAGG  GAGCTCCACC  CACCACCACT  GCTGCTGCAG    540

CTGTGTCATG  TACCGAATCT  GACGAAGGTG  CCAAATGCCA  AGGTGAGGAA  AATGCAAGTT    600

TCTCCCAGGC  CACAACATCC  ACTGAGAGCT  CAGTCAAAGA  TCCTGTAGCC  TGGGAGGCAG    660

GAATGCTGAT  GCACTTCATT  CTACGTAAGT  ATAAATGAG   AGAGCCCATT  ATGAAGGCAG    720

ATATGCTGAA  GGTTGTTGAT  GAAAAGTACA  AGGATCACTT  CACTGAGATC  CTCAATGGAG    780

CCTCTCGCCG  CTTGGAGCTC  GTCTTTGGCC  TTGATTTGAA  GGAAGACAAC  CCTAGTAGCC    840

ACACCTACAC  CCTCGTCAGT  AAGCTAAACC  TCACCAATGA  TGGAAACCTG  AGCAATGATT    900

GGGACTTTCC  CAGGAATGGG  CTTCTGATGC  CTCTCCTGGG  TGTGATCTTC  TTAAAGGGCA    960

ACTCTGCCAC  CGAGGAAGAG  ATCTGGAAAT  TCATGAATGT  GTTGGGAGCC  TATGATGGAG   1020

AGGAGCACTT  AATCTATGGG  GAACCCGTA   AGTTCATCAC  CCAAGATCTG  GTGCAGGAAA   1080

AATATCTGAA  GTACGAGCAG  GTGCCCAACA  GTGATCCCCC  ACGCTATCAA  TTCCTATGGG   1140

GTCCGAGAGC  CTATGCTGAA  ACCACCAAGA  TGAAAGTCCT  CGAGTTTTTG  GCCAAGATGA   1200
```

```
ATGGTGCCAC  TCCCCGTGAC  TTCCCATCCC  ATTATGAAGA  GGCTTTGAGA  GATGAGGAAG    1260

AGAGAGCCCA  AGTCCGATCC  AGTGTTAGAG  CCAGGCGTCG  CACTACTGCC  ACGACTTTTA    1320

GAGCGCGTTC  TAGAGCCCCA  TTCAGCAGGT  CCTCCCACCC  CATGTGAGAA  CTCAGGCAGA    1380

TTGTTCACTT  TGTTTTTGTG  GCAAGATGCC  AACCTTTTGA  AGTAGTGAGC  AGCCAAGATA    1440

TGGCTAGAGA  GATCATCATA  TATATCTCCT  TTGTGTTCCT  GTTAAACATT  AGTATCTTTC    1500

AAGTGTTTTT  CTTTTAATAG  AATGTTTATT  TAGAGTTGGG  ATCTATGTCT  ATGAGCGACA    1560

TGGATCACAC  ATTTATTGGT  GCTGCCAGCT  TAAGCATAA   GAGTTTTGAT  ATTCTATATT    1620

TTTCAAATCC  TTGAATCTTT  TTTGGGTTGA  AGAAGAAGAA  AGCATAGCTT  TAGAATAGAG    1680

ATTTTCTCAG  AAATGTGTGA  AGAACCTCAC  ACAACATAAT  TGGAGTCTTA  AAATAGAGGA    1740

AGAGTAAGCA  AAGCATGTCA  AGTTTTTGTT  TTCTGCATTC  AGTTTTGTTT  TTGTAAAATC    1800

CAAAGATACA  TACCTGGTTG  TTTTTAGCCT  TTTCAAGAAT  GCAGATAAAA  TAAATAGTAA    1860

TAAATT                                                                    1866
```

( 2 ) INFORMATION FOR SEQ ID NO: 2:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
GCTGCGGCTG  CGGGTGTTTC  ATCCACAAAA  TCTAAAAAAG  GTGCCAAGAG  CCACCAAGGT     60

GAGAAAAATG  CAAGTTCCTC  CCAGGCCTCA  ACATCCACTA  AGAGCCCAAG  CGAAGATCCT    120

CTAACCAGGA  AGTCAGGGTC  GTTGGTGCAG  TTCCTGTTGT  ACAAGTATAA  AATAAAAAAG    180

TCCGTTACAA  AGGGAGAAAT  GCTGAAAATT  GTTGGCAAAA  GGTTCAGGGA  GCACTTCCCT    240

GAGATCCTCA  AGAAAGCCTC  TGAGGGCCTC  AGTGTTGTCT  TTGGCCTTGA  GCTGAATAAA    300

GTCAACCCCA  ACGGCCACAC  TTACACCTTC  ATCGACAAGG  TAGACCTCAC  TGATGAGGAA    360

TCCCTGCTCA  GTTCCTGGGA  CTTTCCCAGG  AGAAAGCTTC  TGATGCCTCT  CCTGGGTGTG    420

ATCTTCTTAA  ATGGCAACTC  AGCTACTGAG  GAAGAGATCT  G                         461
```

( 2 ) INFORMATION FOR SEQ ID NO: 3:

( i ) SEQUENCE CHARACTERISTICS:
        ( A ) LENGTH: 476 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
ATCACTGCAA  CTAACAAGAA  AAAAGTATCC  TTTTCATCCC  CTCTTATTTT  GGGGGCTACT     60

ATCCAGAAAA  AGTCTGCTGG  TAGGTCACGT  AGTGCTCTCA  AGAAGCCTCA  GAGAGCACTA    120

TCCACCACTA  CATCTGTAGA  TGTTTCTTAC  AAAAAGTCAT  ACAAGGGAGC  CAACAGCAAA    180

ATTGAGAAAA  AGCAAAGCTT  CTCTCAGGGT  CTATCCTCCA  CTGTGCAGTC  TCACACAGAC    240

CCTCTAACCA  TGAAGACAAA  TATGTTGGTG  CAGTTCCTGA  TGGAAATGTA  CAAGATGAAA    300

AAGCCCATTA  TGAAAGCAGA  TATGCTAAAA  ATTGTCCAAA  AAGCCATAA   GAATTGCTTC    360

CCTGAGATCC  TTAAAAAAGC  TTCTTTCAAC  ATGGAGGTGG  TGTTTGGTGT  TGATTTAAAG    420

AAAGTTGATT  CTACCAAGGA  CTCCTATGTC  CTTGTCAGCA  AAATGGATCT  CCCCAA        476
```

( 2 ) INFORMATION FOR SEQ ID NO: 4:

( i ) SEQUENCE CHARACTERISTICS:
        ( A ) LENGTH: 687 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

| | | | | | | |
|---|---|---|---|---|---|---|
| CATCACCTGC | CCTTCTGCCT | ACACTCCTGC | CTGCTGTGCC | TAACCACAGC | CATCATGCCT | 60 |
| CGGGGTCAGA | AGAGTAAGCT | CCGTGCCCGT | GAGAAACGCC | AGCGGACCCG | TGGTCAGACC | 120 |
| CAGGATCTCA | AGGTTGGTCA | GCCTACTGCA | GCAGAGAAAG | AAGAGTCTCC | TTCCTCTTCC | 180 |
| TCATCTGTTT | TGAGGGATAC | TGCCTCCAGC | TCCCTTGCTT | TTGGCATTCC | CCAGGAGCCT | 240 |
| CAGAGAGAGC | CACCCACCAC | CTCTGCTGCT | GCAGCTATGT | CATGCACTGG | ATCTGATAAA | 300 |
| GGCGACGAGA | GCCAAGATGA | GGAAAATGCA | AGTTCCTCCC | AGGCCTCAAC | ATCCACTGAG | 360 |
| AGATCACTCA | AAGATTCTCT | AACCAGGAAG | ACGAAGATGT | TAGTGCAGTT | CCTGCTGTAC | 420 |
| AAGTATAAAA | TGAAAGAGCC | CACTACAAAG | GCAGAAATGC | TGAAGATCAT | CAGCAAAAAG | 480 |
| TACAAGGAGC | ACTTCCCTGA | GATCTTCAGG | AAAGTCTCTC | AGCGCACGGA | GCTGGTCTTT | 540 |
| GGCCTTGCCT | TGAAGGAGGT | CAACCCCACC | ACTCACTCCT | ACATCCTCGT | CAGCATGCTA | 600 |
| GGCCCCAACG | ATGGAAACCA | GAGCAGTGCC | TGGACCCTTC | CAAGGAATGG | GCTTCTGATG | 660 |
| CCTCTACTGA | GTGTGATCTT | CTTAAAT | | | | 687 |

( 2 ) INFORMATION FOR SEQ ID NO: 5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TAAAAAGGT GCCAAGAGCC AC                                              22

( 2 ) INFORMATION FOR SEQ ID NO: 6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TGAGGCCCTC AGAGGCTTTC                                                20

( 2 ) INFORMATION FOR SEQ ID NO: 7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

AGTCTGCTGG TAGGTCACGT A                                             21

( 2 ) INFORMATION FOR SEQ ID NO: 8:

( i ) SEQUENCE CHARACTERISTICS:
        ( A ) LENGTH: 23 base pairs
        ( B ) TYPE: nucleic acid
        ( C ) STRANDEDNESS: single -continued ( D ) TOPOLOGY: linear ( x i ) SEQUENCE DESCRIPTION: SEQ ID NO: 8:

TCAGGAACTG CACCAACATA TTT                                        23

( 2 ) INFORMATION FOR SEQ ID NO: 9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 9:

AGGGATACTG CCTCCAGCTC                                            20

( 2 ) INFORMATION FOR SEQ ID NO: 10:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO: 10:

CAGGAACTGC ACTAACATCT TC                                         22

( 2 ) INFORMATION FOR SEQ ID NO: 11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 11:

GTGGTGTCCA GCAGTGTCTC                                            20

( 2 ) INFORMATION FOR SEQ ID NO: 12:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO: 12:

GTCAGATTGC CTACATGACA CAG                                        23

1

ISOLATED NUCLEIC ACID MOLECULES WHICH ARE MEMBERS OF THE MAGE-XP FAMILY AND USES THEREOF

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen. The tumor rejection antigen precursors in question do not appear to be closely related to other known tumor rejection antigen precursor coding sequences, and were isolated from the Xp region of human X chromosomes, in contrast to the genes to which they are most closely related, which were found on the Xq region.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774, incorporated by reference in its entirety. The "MAGE" family of tumor rejection antigen precursors is disclosed in this patent.

In U.S. patent application Ser. No. 938,334, now U.S. Pat. No. 5,405,940, Apr. 15, 1995, the disclosure of which is incorporated by reference, it is explained that the MAGE-1 gene codes for a tumor rejection antigen precursor which is processed to nonapeptides which are presented by the HLA-A1 molecule. The nonapeptides which bind to HLA-A1 follow a "rule" for binding in that a motif is satisfied. In this regard, see e.g. PCT/US93/07421; Falk et al., Nature 351: 290–296 (1991); Engelhard, Ann Rev. Immunol. 12: 181–207 (1994); Ruppert et al., Cell 74: 929–937 (1993); Rötzschke et al., Nature 348: 252–254 (1990); Bjorkman et al., Nature 329: 512–518 (1987); Traversari et al., J. Exp. Med. 176: 1453–1457 (1992). The references teach that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993, now abandoned and incorporated by reference, the fact that the MAGE-1 expression product is processed to a second TRA is disclosed. This second TRA is presented by HLA-Cw*1601 molecules. The disclosure shows that a given TRAP can yield a plurality of TRAs, each of which will satisfy a motif rule for binding to an MHC molecule.

In U.S. patent application Ser. No. 994,928, filed Dec. 22, 1992 now abandoned, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 and incorporated by reference herein, an unrelated tumor rejection antigen precursor, the so-called "BAGE" precursor is described. The BAGE precursor is not related to the MAGE family.

In U.S. patent applications Ser. No. 08/096,039 and Ser. No. 08/250,162 now abandoned, both of which are incorporated by reference, non-related TRAP precursor GAGE is also disclosed.

The work which is presented by the papers, patent, and patent applications cited supra deal, in large part, with the MAGE family of genes, and the unrelated BAGE, GAGE and DAGE genes, showing that there are different, additional tumor rejection antigen precursors expressed by cells.

It has now been found that there is yet another family of tumor rejection antigen precursor genes. These nucleic acid molecules show homology to the MAGE family of genes, but this homology is insufficient to identify the members of the Xp family by hybridization with the present members of the MAGE family, as set forth in, e.g., PCT Application PCT/US92/04354 and U.S. Pat. No. 5,342,774, under the conditions of stringency set forth therein. Further, the isolated nucleic acid molecules of the invention were all found on the Xp arm of the X chromosome, as contrasted to the previously identified members of the MAGE family, all of which were found on the Xq arm. Thus, the invention relates to isolated nucleic acid molecules which encode for MAGE-Xp tumor rejection antigen precursors and the uses thereof.

The invention is explained in further detail in the disclosure which follows.

DETAILED DESCRIPTION OF PREFERRED EMBODIMENTS

Example 1

The cosmids D5 and 4965 have been described by Muscatelli, et al., Nature 372: 672–676 (1994), as well as in Muscatelli, et al., Proc. Natl. Acad. Sci. USA 92: 4987–4991 (May 1995) the disclosures of which are incorporated by reference. These cosmids contain portions of the Xp arm of the X-chromosome. The cosmids were digested, using restriction endonucleases EcoRI, BamHI, Hind III, and PstI. Once digested, the DNA was transferred, to a nylon membrane, following agarose electrophoretic migration in an agarose gel.

Following this, a probe, based upon SEQ ID NO: 1, i.e., the sequence for Xp1, was used in hybridization experiments. The probe was approximately 0.45 kilobases in length, and contains 41 base pairs of the first exon (73 base pairs total), the complete second exon, and 299 base pairs of the third (1603 base pairs total). The sequence for what is referred to herein as "Xp1" and is referred to elsewhere as "Xp" may be found in Muscatelli, et al., Proc. Natl. Acad. Sic. USA (May 1995) supra. Further the sequence is found in the EMBL sequence data bank reference to accession number emb X82539, available no later than Feb. 7, 1995.

In order to prepare the 0.4 kb probe, the following primers, i.e., SEQ ID NO: 11 and SEQ ID NO: 12 were used, in PCR, on Xp1 cDNA:

5'-GTGGTGTCCAGCAGTGTCTC-3'

5'-GTCAGATTGCCTACATGACACAG-3

Specifically, the DNA was denatured with NaOH and neutralized in the gel before transfer to a nylon membrane using 20×SSC (SSC=0.15M NaCl, 0.015M sodium citrate, pH 7). Following transfer, the membranes were rinsed for 5 minutes in 6×SSC at room temperature, baked for one hour at 80° C., and pretreated for 4 hours in 6×SSC, 10×Denhardt's solution (0.02% Ficoll, 0.02% polyvinylpyrrolidone, 0.02% BSA), at 65° C.

The membrane was then hybridized in 3.5×SSC, 1×Denhardt's Solution, 25 mm sodium phosphate buffer (pH 7.0), 0.5% SDS, 2 mM EDTA and 3×10$^6$ cpm/ml α $^{32}$P-CTP radiolabelled probe. Hybridization was performed for 18 hours at 65° C. The membrane was then washed at 65° C., four times, for one hour each time in 2×SSC, 0.5% SDS, 1×Denhardt's solution; once for 30 minutes at 0.2×SSC, 0.1% SDS; and once for 30 minutes in 0.1×SSC, 0.1% SDS. The membranes were autoradiographed using Kodak X-ARS film, and Kodak X-Omatic fine intensifying screens.

Following the hybridization, several signals of differing intensity were observed. Of these, three EcoRI fragments from cosmid 4965, which were 1.5, 2.2, and 2.5 kilobases in length were isolated, and cloned into vector pTZ19R for sequencing. Partial sequencing showed that each fragment contained a sequence homologous to the third exon of Xp1. Homology of the three sequences, relative to Xp1, was 75%, 60%, and 80%, for genes referred to hereafter as MAGE-Xp2, MAGE-Xp3, and MAGE-Xp4. These are presented in SEQ ID NOS: 2, 3 and 4, respectively.

The foregoing disclosure, places many tools of extreme value in the hands of the skilled artisan. To begin, the examples identify isolated nucleic acid molecules which code for MAGE-Xp tumor rejection antigen precursors as well as the nucleic acid molecules complementary thereto. It is known that DNA exists in double stranded form, and that each of the two strands is complementary to the other. Nucleic acid hybridization technology has developed to the point where, given a strand of DNA, the skilled artisan can isolate its complement, or synthesize it. The invention includes, inter alia, the phenomenon of double strandedness to permit the artisan to identify the X chromosome, especially the Xp element, as well as defects in the chromosome.

Such assays can be carried out by one of ordinary skill in the art, using standard methodologies. For example, using the well known polymerase chain reaction (PCR), one uses the following primers:

For identifying Xp2:

| | |
|---|---|
| 5'-TAAAAAAGGTGCCAAGAGCCAC-3' | (SEQ ID NO: 5); |
| 5'-TGAGGCCCTCAGAGGCTTT'3- | (SEQ ID NO: 6). |

For identifying Xp3:

| | |
|---|---|
| 5'-AGTCTGCTGGTAGGTCACGTA-3' | (SEQ ID NO: 7); |
| 5'-TCAGGAACTGCACCAACATATTT-3' | (SEQ ID NO: 8). |

For identifying Xp4:

| | |
|---|---|
| 5'-AGGGATACTGCCTCCAGCTC-3' | (SEQ ID NO: 9); |
| 5'-CAGGAACTGCACTAACATCTTC-3' | (SEQ ID NO: 10). |

One uses these primers in accordance with standard PCR protocols which need not be repeated here.

"Nucleic acid molecule" as used herein refers to all species of DNA and RNA which possess the properties discussed supra. Genomic and complementary DNA, or "cDNA" both code for particular proteins, and as the examples directed to isolation of MAGE coding sequences show, this disclosure teaches the artisan how to secure both of these.

All isolated nucleic acid molecules which encode MAGE-Xp proteins, with the exception of MAGE-Xp1, are encompassed by this invention. This includes those nucleic acid molecules which hybridize to any of MAGE-Xp2, MAGE-Xp3, or MAGE-Xp4 under stringent conditions. As used herein, this refers to conditions such as hybridization with 5×10$^6$ cpm/ml for 18 hours at 65° C., followed by 4, 20 minute washes at 65° C. with each wash using 2×SSC, 0.5% SDS and 1×Denhardt's solution, followed by two washes at 0.2×SSC, 1% SDS (20 minutes, each wash), and, finally, two washes at 68° C., 1% SDS, a varying concentration of SSC, each of these washes being for 20 minutes. The final concentration of SSC should be no greater than 0.5×SSC, more preferably it is 0.2×SSC, and most preferably it is 0.1×SSC.

Similarly, RNA molecules, such as mRNA can be secured. Again, with reference to the skilled artisan, once one has a coding sequence in hand, mRNA can be isolated or synthesized.

Complementary sequences which do not code for TRAPs, such as "antisense DNA" or mRNA are useful, e.g., in probing for the coding sequence as well as in methodologies for blocking its expression.

It will also be clear that one may manufacture biologically pure cultures of prokaryotic and eukaryotic cell lines which have been transferred or transfected with nucleic acid sequences which code for or express the MAGE-Xp molecules. Such cultures can be used as a source for tumor rejection antigens, e.g., or as therapeutics. This aspect of the invention is discussed infra.

Cells transfected with the MAGE-Xp coding sequences may also be transfected with other coding sequences. Examples of other coding sequences include cytokine genes, such as interleukins (e.g., IL-2 or IL-4), or major histocompatibility complex (MHC) or human leukocyte antigen (HLA) molecules. Cytokine gene transfection is of value because expression of these is expected to enhance the therapeutic efficacy of the biologically pure culture of the cells in vivo. The art is well aware of therapies where interleukin transfectants have been administered to subjects for treating cancerous conditions. In a particularly preferred embodiment, cells are transfected with sequence coding for each of (i) MAGE-Xp molecule, (ii) an HLA/MHC molecule, and (iii) a cytokine.

Transfection with an MHC/HLA coding sequence is desirable because certain of the TRAs derived from MAGE-Xp may be preferentially or especially presented only by particular MHC/HLA molecules. Thus, where a recipient cell already expresses the MHC/HLA molecule associated with presentation of a TRA, additional transfection may not be necessary although further transformation could be used to cause overexpression of the antigen. On the other hand, it may be desirable to transfect with a second sequence when the recipient cell does not normally express the relevant MHC/HLA molecule. It is to be understood, of course, that transfection with one additional sequence does not preclude further transfection with other sequences.

The term "biologically pure" as used in connection with the cell line described herein simply means that these are essentially free of other cells. Strictly speaking, a "cell line" by definition is "biologically pure", but the recitation will establish this fully.

Transfection of cells requires that an appropriate vector be used. Thus, the invention encompasses expression vectors where a coding sequence for the MAGE-Xp TRAP of interest is operably linked to a promoter. The promoter may be a strong promoter, such as those well known to the art, or a differential promoter, i.e., one which is operative only in specific cell types. The expression vectors may also contain all or a part of a viral or bacterial genome, such as vaccinia virus or BCG. Such vectors are especially useful in preparing vaccines.

The expression vectors may incorporate several coding sequences, as long as the MAGE-Xp sequence is contained therein. The cytokine and/or HLA genes discussed supra may be included in a single vector with the TRAP sequence. Where this is not desired, then an expression system may be provided, where two or more separate vectors are used where each coding sequence is operably linked to a promoter. Again, the promoter may be a strong or differential promoter. Co-transfection is a well known technique, and the artisan in this field is expected to have this technology available for utilization. The vectors may be constructed so that they code for the TRA molecule directly, rather than the MAGE-Xp TRAP. This eliminates the need for post-translational processing.

As the foregoing discussion makes clear, the sequences code for "tumor rejection antigen precursors" ("TRAPs") which, in turn, are processed into tumor rejection antigens ("TRAs"). Perhaps their most noteworthy aspect is as vaccines for treating various cancerous conditions. The evidence points to presentation of TRAs on tumor cells, followed by the development of an immune response and deletion of the cells. The evidence in the art shows that when various TRAs are administered to cells, a CTL response is mounted and presenting cells are deleted. This is behavior characteristic of vaccines, and hence TRAPs, which are processed into TRAs, and the TRAs themselves may be used, either alone or in pharmaceutically appropriate compositions, as vaccines. Similarly, presenting cells may be used in the same manner, either alone or as combined with ingredients or yield pharmaceutical compositions. Additional materials which may be used as vaccines include isolated cells which present the TRA molecule on their surface, as well as TRAP fragments, mutated viruses, especially etiolated forms, and transformed bacteria. "Fragments" as used herein refers to peptides which are smaller than the TRA, but which possess the properties required of a vaccine, as discussed supra. Another vaccine comprises or consists of complexes of TRA and HLA molecule. Vaccines of the type described herein may be used preventively, i.e., via administration to a subject in an amount sufficient to prevent onset of a cancerous condition.

The generation of an immune response, be it T-cell or B-cell related, is characteristic of the effect of the presented tumor rejection antigen. With respect to the B-cell response, this involves, inter alia, the generation of antibodies to the TRA, i.e., which specifically bind thereto. In addition, the TRAP molecules are of sufficient size to render them immunogenic, and antibodies which specifically bind thereto are a part of this invention. These antibodies may be polyclonal or monoclonal, the latter being prepared by any of the well recognized methodologies for their preparation which need not be repeated here. For example, mAbs may be prepared using an animal model, e.g., a Balb/C mouse or in a test tube, using, e.g., EBV transformants. In addition, antiserum may be isolated from a subject afflicted with a cancerous condition where certain cells present a TRA. Such antibodies may also be generated to epitope defined by the interaction of TRA and HLA/MHC molecules.

Review of the foregoing disclosure will show that there are a number of facets to the system which may be referred to as "tumor rejection antigen presentation and recognition". Recognition of these phenomena has diagnostic consequences. For example, the existence of specific CTL clones, or antibodies to the TRA makes it possible to diagnose or monitor cancerous conditions (explained infra), by monitoring the CTLs in a sample from a subject, binding of antibodies to TRAs, or the activity of anti-TRA CTLs in connection with subject samples. Similarly, the expression of nucleic acid molecules for TRAPs can be monitored via amplification (e.g., "polymerase chain reaction"), anti-sense hybridization, probe technologies, and so forth. Various subject samples, including body fluids (blood, serum, and other exudates, e.g.), tissues and tumors may be so assayed.

A particular manner of diagnosis is to use an adaptation of the standard "tuberculin test" currently used for diagnosis of tuberculosis. This standard skin test administers a stable form of "purified protein derivative" or "PPD" as a diagnostic aid. In a parallel fashion, TRAs in accordance with this invention may be used in such a skin test as a diagnostic aid or monitoring method.

The term "cancerous condition" is used herein to embrace all physiological events that commence with the initiation of the cancer and result in final clinical manifestation. Tumors do not spring up "ab initio" as visible tumors; rather there are various events associated with the transformation of a normal cell to malignancy, followed by development of a growth of biomass, such as a tumor, metastasis, etc. In addition, remission may be conceived of as part of "a cancerous condition" as tumors seldom spontaneously disappear. The diagnostic aspects of this invention include all events involved in carcinogenesis, from the first transformation to malignancy of a single cell, through tumor development and metastasis, as well as remission. All are embraced herein.

Where "subject" is used, the term embraces any species which can be afflicted with a cancerous condition. This includes humans and non-humans, such as domesticated animals, breeding stock, and so forth.

There are therapeutic aspects of this invention as well. The efficacy of administration of effective amounts of TRAPs and TRAs as vaccines have already been discussed supra. Similarly, one may develop the specific CTLs in vitro and then administer these to the subject. Antibodies may be administered, either polyclonal or monoclonal, which specifically bind to cells presenting the TRA of interest. These antibodies may be coupled to specific antitumor agents, including, but not being limited to, methotrexate radioiodinated compounds, toxins such as ricin, other cytostatic or cytolytic drugs, and so forth. Thus, "targeted" antibody therapy is included herein, as is the application of deletion of the cancerous cells by the use of CTLs.

The terms and expression which have been employed are used as terms of description and not of limitation, and there is no intention in the use of such terms and expression of excluding any equivalents of the features shown and described or portions thereof, it being recognized that various modifications are possible within the scope of the invention.

---

We claim:

1. Isolated nucleic acid molecule which encodes a MAGE-Xp tumor rejection antigen precursor or is complementary to an isolated nucleic acid molecule which encodes a MAGE-Xp tumor rejection antigen precursor, wherein said isolated nucleic acid molecule (i) is not SEQ ID NO: 1, and (ii) hybridizes to at least one isolated nucleic acid molecule consisting of SEQ ID NO: 2, SEQ ID NO: 3, and SEQ ID NO: 4, under stringent conditions.

2. Isolated nucleic acid molecule selected from the group consisting of the isolated nucleic acid molecule consisting of the nucleotide sequence of SEQ ID NO: 1, the isolated nucleic acid molecule consisting of the nucleotide sequence of SEQ ID NO: 2, and the isolated nucleic acid molecule consisting of the nucleotide sequence of SEQ ID NO: 3.

3. The isolated nucleic acid molecule of claim 2, consisting of SEQ ID NO: 2.

4. The isolated nucleic acid molecule of claim 2, consisting of SEQ ID NO: 3.

5. The isolated nucleic acid molecule of claim 2, consisting of SEQ ID NO: 4.

6. Expression vector comprising the isolated nucleic acid molecule of claim 2, operably linked to a promoter.

7. Eukaryotic cell line transfected with the isolated nucleic acid molecule of claim 2.

8. Prokaryotic cell strain transformed with the isolated nucleic acid molecule of claim 2.

9. Method for identifying human X chromosome in a sample comprising contacting said sample with the isolated nucleic acid molecule of claim 1 under condition favoring hybridization of said isolated nucleic acid molecule to said X chromosome, and determining hybridization as a determination of said human X chromosome.

10. Isolated nucleic acid molecule selected from the group consisting of SEQ ID NO: 5, SEQ ID NO: 6, SEQ ID NO: 7, SEQ ID NO: 8, SEQ ID NO: 9, and SEQ ID NO: 10.

11. Kit useful in a polymerase chain reaction based assay, comprising one of:

(i) SEQ ID NO: 5 and SEQ ID NO: 6, (ii) SEQ ID NO: 7 and SEQ ID NO: 8, and (iii) SEQ ID NO: 9 and SEQ ID NO: 10.

12. Method for determining transcription of a MAGE-Xp gene in a sample, comprising contacting said sample with at least one of (i) SEQ ID NO: 5 and SEQ ID NO: 6, (ii) SEQ ID NO: 7 and SEQ ID NO: 8, and (iii) SEQ ID NO: 9 and SEQ ID NO: 10, under conditions favoring hybridization of (i) (ii) or (iii) to mRNA or cDNA of a MAGE-Xp gene, carrying out polymerase chain reaction and determining an extension product of said polymerase chain reaction to determine transcription of said MAGE-Xp gene in said sample.

* * * * *